US008715201B2

(12) United States Patent
Koehler et al.

(10) Patent No.: US 8,715,201 B2
(45) Date of Patent: May 6, 2014

(54) DETECTION OF BODY SOUNDS

(75) Inventors: Ulrich Koehler, Marburg (DE); Volker Gross, Wettenberg (DE)

(73) Assignee: Heinen + Lowenstein GmbH & Co. KG (DE)

( * ) Notice: Subject to any disclaimer, the term of this patent is extended or adjusted under 35 U.S.C. 154(b) by 1701 days.

(21) Appl. No.: 12/092,349

(22) PCT Filed: Oct. 25, 2006

(86) PCT No.: PCT/EP2006/010295
§ 371 (c)(1),
(2), (4) Date: Jul. 8, 2008

(87) PCT Pub. No.: WO2007/051556
PCT Pub. Date: May 10, 2007

(65) Prior Publication Data
US 2008/0306367 A1    Dec. 11, 2008

(30) Foreign Application Priority Data
Nov. 4, 2005    (DE) .......................... 10 2005 053 109

(51) Int. Cl.
*A61B 5/08*    (2006.01)

(52) U.S. Cl.
USPC .......................................................... 600/529

(58) Field of Classification Search
USPC .......................................... 600/529, 364, 586
See application file for complete search history.

(56) References Cited

U.S. PATENT DOCUMENTS

2002/0013538 A1    1/2002    Teller
2002/0151789 A1    10/2002    Mansy et al.
(Continued)

FOREIGN PATENT DOCUMENTS

DE    19960014 B4    6/2001
DE    102004059228 B3    8/2006
(Continued)

OTHER PUBLICATIONS

Homs-Corbera et al, "Algorithm for time-frequency detection and analysis of wheezes"; Proceedings of the 22$^{nd}$ Annual International Conference of the IEEE Engineering in Medicine and Biology Society, 2000; vol. 4, pp. 2977-2980; Jan. 12, 2005; XP002459683.

(Continued)

*Primary Examiner* — Christine Matthews
(74) *Attorney, Agent, or Firm* — Sheridan Ross P.C.

(57) ABSTRACT

Disclosed is a method for detecting and monitoring body sounds in humans and animals, in which bioacoustic sensors and analyzers that are mounted downstream are used for the stationary or mobile long-term monitoring of intensive care patients' respiration, for example. The patients' lung sounds are detected and stored along with measured data which are available right away especially for the early detection of diseases and acute disturbances. Adequately monitoring intestinal sounds makes it possible to evaluate peristalsis and detect mechanical/paralytic ileus early on. An early warning system for the clinical sector immediately generates signals allowing doctors and nurses to take rapid action in case of an emergency. The inventive apparatus requires a maximum of only three bioacoustic sensors (12), each of which can be fixed to a point of an object body (K) facing the object, a maximum of one sensor (14) for recording surrounding noises, a maximum of four separable channels (11) for recording and transmitting sound signals or sound data detected by the sensors (12), and devices for supplying power and forwarding, converting, storing, and displaying sequences of signals or data on or in a recorder or a computer unit (20).

27 Claims, 5 Drawing Sheets

(56) References Cited

U.S. PATENT DOCUMENTS

2004/0225226 A1    11/2004    Lehrman et al.
2005/0165323 A1    7/2005    Montgomery et al.

FOREIGN PATENT DOCUMENTS

| EP | 0951867 | A | 10/1999 |
| EP | 0883877 | | 12/2004 |
| EP | 1495721 | A | 1/2005 |
| WO | WO03/000015 | A2 | 3/2001 |
| WO | WO01/19243 | A1 | 1/2003 |
| WO | WO2004/002317 | A | 1/2004 |

OTHER PUBLICATIONS

International Search Report of the European Patent Office dated Nov. 23, 2007 for International Application No. PCT/EP2006/010295; Applicants, Koehler et al.

Zaknich et al., "A Real-Time for the Classification of Sheep feeding Phases from Acoustic Signals of Jaw Sounds," Australian Journal of Intelligent Inform. Process. Syst., Winter 1998, pp. 103-110.

DETECTION OF BODY SOUNDS

CROSS REFERENCE TO RELATED APPLICATIONS

This application is a national stage application under 35 U.S.C. 371 of PCT Application No. PCT/EP2006/010295 having an international filing date of 25 Oct. 2006, which designated the United States, which PCT application claimed the benefit of German Application No. 102005053109.1 filed 4 Nov. 2005, the entire disclosure of which is hereby incorporated herein by reference.

The invention relates to a method and an apparatus for detecting and monitoring body sounds in humans and animals according to the generic part of claims 1, 9, 12, and 14.

The stethoscope, in which hose pipes lead from an acoustic pick-up capsule to earphones, usually used for auscultating body sounds, is generally known. With it, sound phenomena of heart, lungs, abdomen, thyroid gland, etc. are observed, in order to detect and diagnose conspicuities.

With acoustic transducers, identification signals enabling an analysis can be generated. U.S. Pat. No. 5,259,373, for example, discloses a respirator with which pressure variations can be registered. According to DE 101 59 384, an acoustic pick-up, whose signals allow to draw conclusions to the condition of the lungs, is arranged in the gas feed system. The evaluation is effected by means of a comparison with known sound or noise patterns, to detect, for example, a secretion stasis.

EP 0504 945 A2 discloses a mobile device which allows to record the pulse frequency, respiratory sounds and the saturation of the blood with oxygen by means of a position transducer, electrodes, a larynx microphone and a finger sensor, taking into account the position of the body. The data stored are analyzed by means of a computer to determine existence and seriousness of a sleep apnoea syndrome. Further examinations are not provided or involve uncertainties.

U.S. Pat. No. 6,261,238 B1 provides a so-called phonopneumographic system for recording and analyzing, above all, respiratory sounds of mammals including humans. It requires great expenditure and needs, for detecting and analyzing various types of sounds, quite a number of respiration sensors and devices mounted downstream for signal transmission and amplification including digitization for the purpose of processing in a computer with monitor and printer. Furthermore, storing and listening devices are provided. The system presupposes a detection of the respiratory phases and requires a multitude of spectral-curve matchings with individual computation of each curve, i.e. numerous seral steps with high computing intensity for recording and analyzing the measured values. The monitoring at night during 8 hours requires, e.g., 8×60×60×20=576,000 individual computations. The first classification may strongly influence or upset the precision of the following steps. If a sound is initially classified falsely as a background sound, no further analysis will take place.

Furthermore, the conventional systems often have the disadvantage that relatively many sensors are required, e.g. six acoustic sensors, about whose arrangement in space or distribution on an object body, only insufficient information is given.

It is an important objective of the invention to considerably simplify observation, recording and analysis of body sounds in humans and animals. With economical means, it shall be possible to reliably identify and assess the occurrence of anomalies, without restrictions as to place and time of the day, it being possible to carry out long-term measurements and records of respiratory sounds, also and above all during the night. It is another objective to develop a versatile, mobile equipment which is easy to operate.

The main features of the invention are described in claims 1, 9, 12, and 14. Embodiments are the subject matter of claims 2 to 8, 10, 11, 13, and 15 to 27.

A method for detecting and monitoring body sounds in humans and animals, using bioacoustic sensors and analyzers that are mounted downstream is characterized according to the invention, according to claim 1, by the fact
that bioacoustic sensors are fixed to a maximum of three points of an object body,
that a maximum of one additional bioacoustic sensor is provided for recording surrounding noise,
that the bioacoustic sensors continuously detect sound signals and/or sound data, within a selectable time segment,
that the sequences of sound signals and/or sound data generated in this manner are digitized, stored, and converted into frequency-dependent spectral curves,
that node-defined matching lines continuously allocated to the spectral curves are developed, and
that the matching lines are compared with the corresponding spectral curves for analyzable and signalizable identification of specific sound symptoms, e.g. wheezing, ronchus, cough, or the like.

Therefore, contrary to the state of the art, it is possible, to monitor, e.g., the respiration course of a proband non-invasively, not only during the day, but also, above all, during the night and in periods of many hours, even in a mobile manner. This can easily be carried out even with infants and mammals, who are not able to follow any instructions. The long-term measuring results and curve comparisons provide, furthermore, conclusive or at least limitable actual values and patterns from which disease-specific symptoms and reliably be objectivated. For this purpose, it is not necessary (unlike conventional devices) to positively identify a sound in advance as a real or pure sound of a mammal respiratory system. It is also sufficient for detecting loudness-dependent characteristics to just compare the amplitudes of individual sound channels. Sounds outside the respective frequency range of interest are eliminated, e.g., by means of an analog band-pass filter.

The individual conversion time windows are advantageously selected, e.g., for the analysis of respiratory sounds, in such a way that resolutions of approx. 0.1 s result. To obtain frequency-specific characteristics, it is advantageous to effect a fast Fourier transform of the data in the spectral range, one spectral curve per conversion time window originating, with which amplitudes are represented over the frequency and recorded.

According to a development of the invention, at least two frequency ranges are selected from each spectral curve and the medians of the amplitudes which correspond to node values of a matching line are determined, whereupon allocated matching lines are developed on the basis of node values, namely by their linear or quasi-linear connection. In an X, Y-coordinate axis system, the node values are Y-amounts at a frequency X, which corresponds to the middle as to time of the respective frequency range.

To refine the method, one can select at least one third, preferably medium, frequency range, thus introducing further nodes for more precise matching lines. In this way, one obtains a very good basis for the continuous control and analysis, without requiring an excessive computation effort.

To search for local maxima, one compares the Y-values of the spectral curve with the Y-values of the matching line, formulating a threshold-value criterion. Identification will be effected if the local maximum in the spot X exceeds a threshold value in such a way that the Y-value of the spectral curve is higher than the sum of the Y-value of the matching line and a basic constant K1. The latter is preset according to experimental values gained from statistically secured series of measurements.

It is particularly advantageous if instead of only the basic constant K1, a term consisting of a share constant K2 and the median of the deviations of the spectral curve from the matching line, multiplied by a dynamic factor, is added, so that then, the Y-value of the spectral curve is higher than the sum of the Y-value of the matching line and the share constant K2 as well as a dynamic constant K3, multiplied by the median of the deviations of the spectral curve from the matching line.

For analyzing wheezing in humans, one selects, in an advantageous embodiment of the method, at the ends of a range of 150 Hz to 1,600 Hz, two partial frequency ranges whose scope is given by a factor of a specifiable peak criterion for the selection of the local maxima, e.g. a frequency width of 100 Hz. This factor may be, for example, 1 or 2. For an even better adaptation of the method to the human and his respiratory sounds, a further node is formed in a third frequency range within the spectral curve, e.g. at approx. 700 Hz for respiratory sounds of adults; for children, a somewhat higher frequency is chosen.

In a preferred exemplary embodiment, which reliably identifies significant wheezing phenomena, the search for local maxima is followed, according to claim 9, by the application of plausibility criteria based on secured measuring results, in particular as follows:
  i) the local maximum in the frequency range within a conversion time window is not wider than 100 Hz when the threshold-value criterion is exceeded;
  ii) the maxima detected lie within a frequency band between 150 Hz and 1,600 Hz;
  iii) the frequency change of the strongest of the local maxima (dominant frequency) is less than 100 Hz between two successive conversion time windows;
  iv) the wheezing events have a minimum length of more than 0.3 s, i.e. they occur, in case of a resolution as to time of 0.1 s, in at least four successive conversion time windows;
  v) the wheezing events do not last longer than double the time of a normal mean expiration phase of the mammal genus in question (which lasts approx. 4 s in humans).

Afterwards, a combined wheezing rate can be obtained for each diagnosis time segment, e.g. 30 s or a complete breath, by combining the wheezing detected by all body sensors, the rate relating to the time portion of all events which were detected by at least one sensor. If a loud signal appears simultaneously in the external channel only, it will be most probably a surrounding noise and the signal will be discarded as being an artifact.

For cough detection, the occurrence of steep edges of the amplitude signal of the surrounding noise is analyzed, according to claim 11, if simultaneously large amplitudes or overshootings are detected in all other sound signals facing the object body. Cough sequences can be formed and stored, preferably with summation as well as averaging over the entire measuring time and/or through time-dependency diagrams of the maximum values.

An apparatus for detecting and monitoring body sounds in humans and animals, using bioacoustic sensors and analyzers that are mounted downstream, in particular for carrying out the method according to any of claims 1 to 13, includes according to the invention, according to claim 14, a maximum of three bioacoustic sensors, each of which can be fixed to an examination area facing the organ system to be monitored of an object body, as well as a sensor for recording the surrounding noises, a maximum of four separable channels for recording and transmitting the sound signals or sound data detected by the sensors, and devices for supplying power and forwarding, converting, storing, and displaying sequences of signals or data supplied by the sensors on or in a recorder or a computer unit. Devices for the Fourier transform or fast Fourier transform may exist in the form of PC-installed software. In addition to transmission lines or radio transmission means as well as the recorder and/or computer, only a—preferably integrated—analog/digital converter is required, which may also be accommodated in sensor housings or may be in telecontrol connection with the sensors. That means that the overall system is simple and, therefore, cost-advantageous, but efficient. It can be used in a mobile manner and is very practical because its handling creates no problems.

Surprisingly, it was found that for monitoring the respiratory sounds, it is sufficient to fix a maximum of three acoustic body sensors, placed near the trachea and in the area of each pulmonary lobe, preferably approximately in the middle above each pulmonary lobe or below the scapula and (with humans) in the intercostal space between the 5th and 7th ribs. Thus, the expenditure of apparatus is greatly reduced as compared with conventional devices and, at the same time, the reliability of use is enhanced. To record and exclude noises which are irrelevant for the examination, an ambient sensor is expediently provided in addition, which can be fixed, e.g., on a sensor-cable box or on the back of a tracheal sensor. In addition, a sensor for scanning the movements of the thorax, in particular for recording the respiratory activity, can be provided.

That means that the apparatus requires for recording and transmitting the sound signals or sound data altogether only up to four separable or separated channels whose recordings can be evaluated and analyzed automatically and/or audio-visually. On or in the bioacoustic sensors or in telecontrol connection therewith, analog/digital converters are provided whose output supplies digital signals or signal sequences, which are forwarded by means of at least one transmitter coupled with a data memory and/or a transfer device.

For a relatively comfortable wearing of the bioacoustic sensors, a neck and/or chest belt or the like, possibly including shoulder straps and/or Velcro fasteners, can be used. Suitable acoustic sensors are, above all, air-coupled or piezo microphones, which can be fixed on the object body at selected points, e.g. by means of adhesive film or plaster, but can also be integrated in a chest belt.

In a manner known per se, the basic equipment can be supplemented, for example by a position sensor, a motion sensor for the thorax and/or a sensor for the oxygen content of the blood, which is fixed, e.g., on an ear or on an extremity. Furthermore, to increase the sensitivity and as a security against disturbances, pre-amplifiers and analog filters, especially band-pass filters, can be provided.

Such, or all, aids can be accommodated in a small housing. It is favorable to design the housing as a (signal) data logger, portable on the body or else integrated, which does not need to be a separate device, but may be part of an analysis station or a sleep center, and which is preferably equipped, for monitoring body sounds and recording the signals of a maximum of four sound channels, with acoustic micromemories, e.g. with two stereo mini units in the manner of MP3 recorders.

Further features, details and advantages of the invention are evident from the wording of the claims as well as from the following description of exemplary embodiments by means of the drawings, in which:

Figure 1:
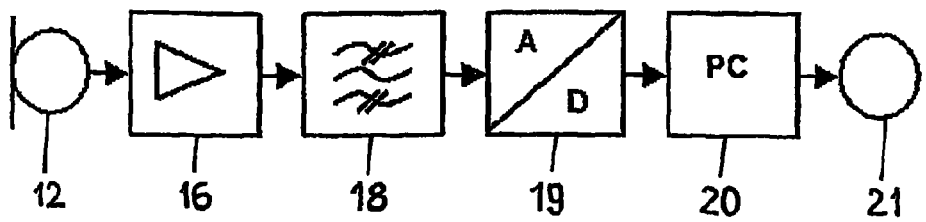
FIG. 1 is a diagram of a measuring chain.

An apparatus according to the invention for detecting and monitoring body sounds in humans and animals includes only few components, namely bioacoustic sensors and analyzing aids that are mounted downstream, which can all be accommodated in a small housing. Therefore, the apparatus, also called data logger, generally designated with 10, can, therefore, be used in a mobile manner. It requires a maximum of three acoustic sensors 12, which can be fixed on selected points of the body, e.g. by means of adhesive films. FIG. 1 shows the structure of a typical measuring chain. A sensor 12 transmits signals to the amplifier 16, the filter unit 18, preferably designed as a band-pass filter, being mounted downstream thereof. The output signals of the filter unit are digitized in at least one analog/digital converter 19 and fed in this form to the storage/computer unit 20 (e.g. memory cards whose data are afterwards evaluated in a computer). In addition, an ambient sensor 14 can be provided and can be connected by means of cables 15 (FIG. 9) with a box in which the amplifier 16 as well as the filter 18 mounted downstream and the analog-digital converter 19 are housed. The further main component in the form of the storage medium 20 can be accommodated directly in the housing or be connected with it by cable or radio.

The three acoustic sensors 12, which can be air-coupled or piezo microphones, are fixed, e.g. by means of the adhesive films, on the object body K (FIG. 7), namely one (31) in the area of the trachea and two (25 in FIG. 8) in the area of each pulmonary lobe, preferably approximately in the middle above each pulmonary lobe or below the scapula and, with humans, in the intercostal space between the 5th and 7th ribs. The sensor 12 or 31, respectively, arranged near the trachea, may carry on its back the ambient sensor 14, e.g. on a common neck belt 32 (see FIG. 7). The holding device on the upper part of the body K advantageously supports a chest belt 22, which—in so far similar to a brassiere—may have shoulder straps 23 and can help to relieve the weight for the sensors 12, 14 including their cables 15. Possibly, a motion sensor 33 for the thorax and/or a position sensor is provided, and, furthermore, if necessary, a blood-$O_2$ sensor to be fixed, e.g., on the ear or on an extremity.

The amplifier 16 can be arranged in housings of the sensors 12, 14 or be in telecontrol connection with them. The analog-digital converter 19 is followed by a transfer device, e.g. in the form of an electric line or a radio link, leading on a short or long way to the data memory or to the evaluation unit 20, because the latter is not necessarily arranged in the same room; according to the given local conditions it can be arranged near or far away the system can be connected with communication networks and is completed by at least one energy supplier (not shown), which may consist in a manner known per se of a power pack or an accumulator or battery block.

Figure 2:
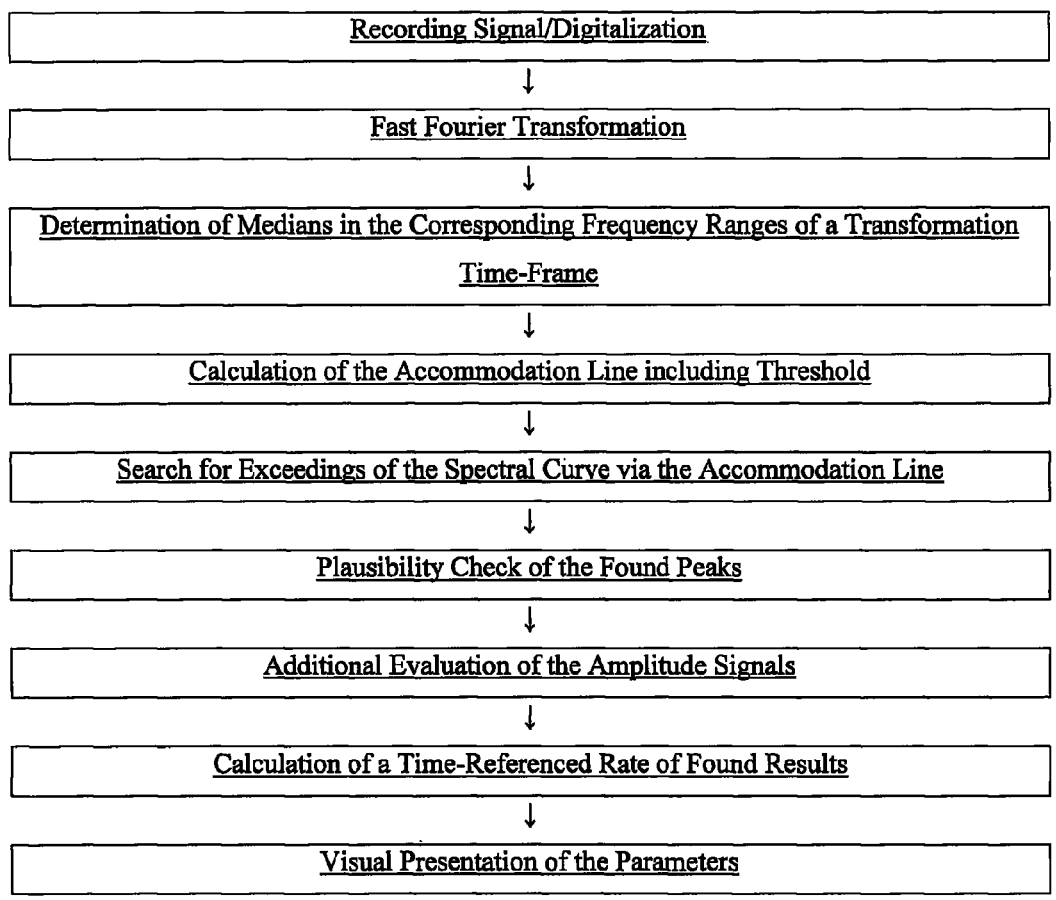
FIG. 2 is a block flowchart of the method according to the invention.

From FIG. 2, the typical steps of the method according to the invention are evident. They can be programmed in this or a similar sequence in a relatively simple and clear manner.

Figure 3:
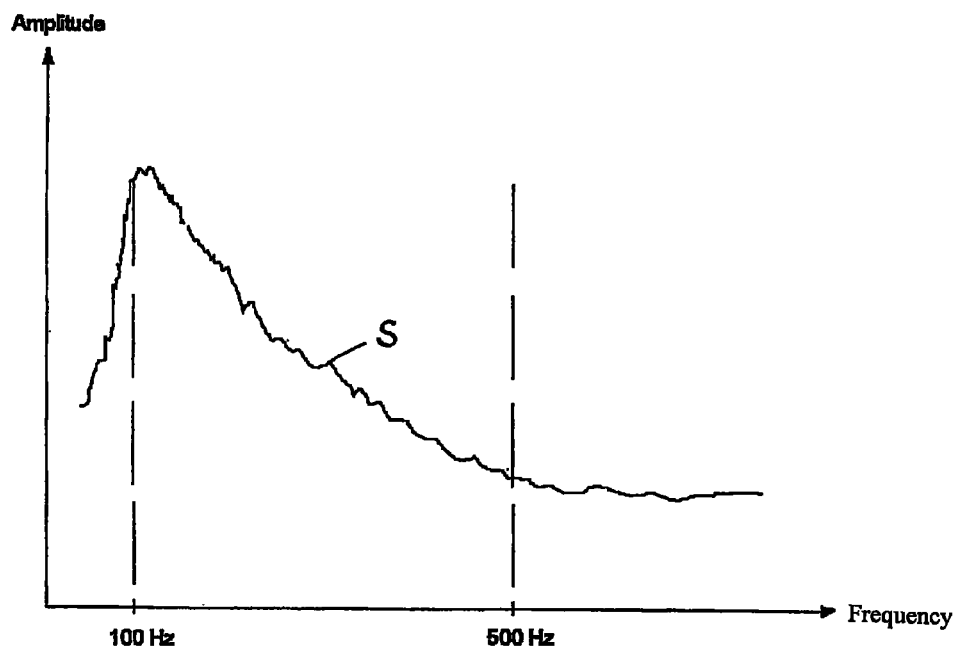
FIG. 3 is a typical spectral curve of a conversion time window.

FIG. 3 shows a typical spectral curve S of a conversion time window during respiration of an adult human, the relative signal amplitude being plotted over the frequency. It is clearly visible that a maximum exists at or slightly above 100 Hz, whereas sounds of higher frequency diminish as from about 500 Hz towards a low value.

Figure 4:
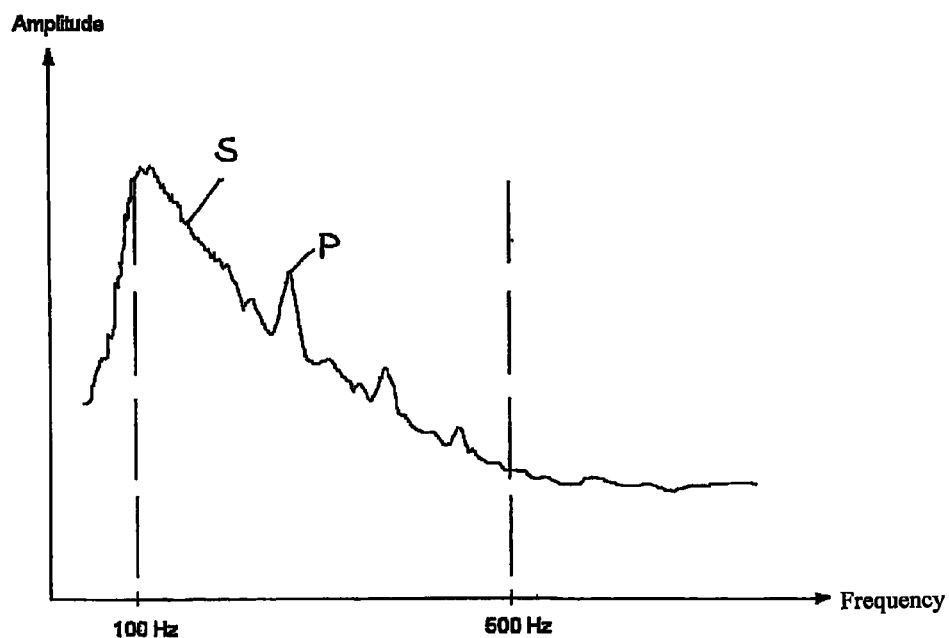
FIG. 4 is a spectral curve similar to FIG. 3, but with local maxima.

FIG. 4 shows a comparable spectral curve S, the respiration of an adult showing local maxima in a middle range—here, between about 200 Hz and 500 Hz. A wheezing event corresponds to a peak value or main peak P; harmonic components indicate reduced peak values.

Figure 5:
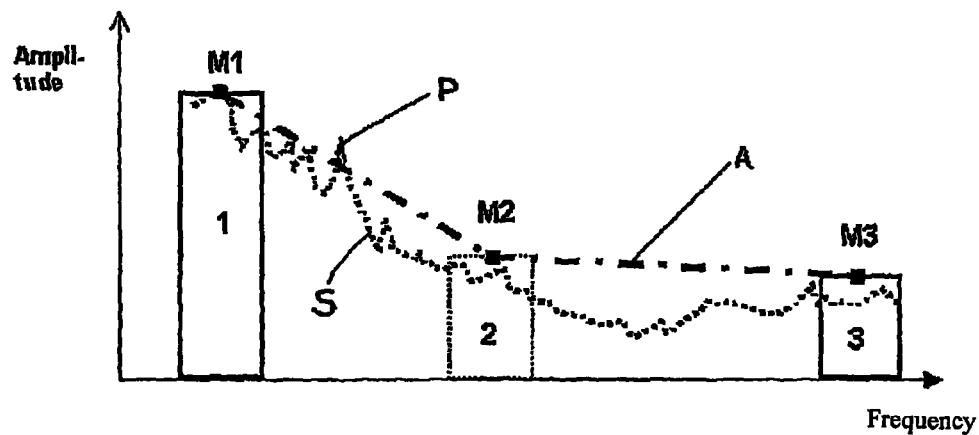
FIG. 5 is a spectral curve similar to FIG. 4, but with a matching line and with curve nodes.
Figure 6:
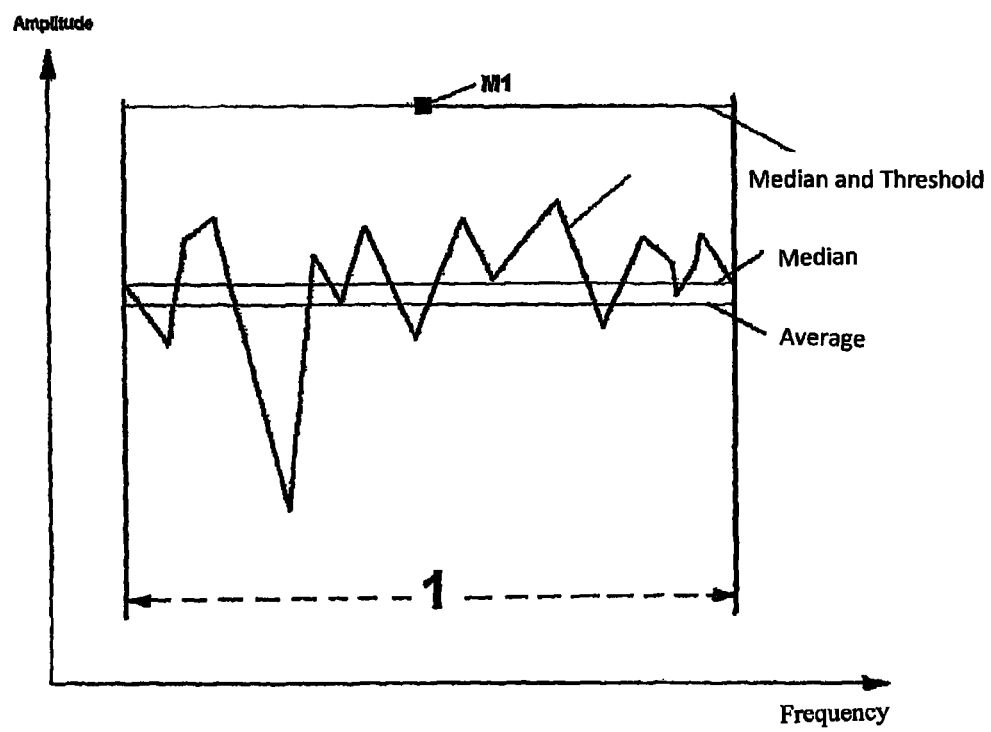
FIG. 6 is a detail of a node curve with median and average values.

The analysis according to the invention uses median-based nodes, as shown in FIGS. 5 and 6. In the example of a normal respiration of an adult with wheezing, a spectral curve S has a main peak P between two curve nodes $M_1$ and $M_2$. A calculated matching line A, to which a threshold value has already been added, lies in general above the spectral curve S, whose main peak P, however, projects over the matching line A (including the threshold value).

FIG. 6 shows schematically in which way a section of a spectral curve in a selected lower frequency range "1" is used for obtaining a node value $M_1$. This value is the sum of a threshold value and the median value of the spectral curve S, which in the example shown lies above the average value and characterizes the curve in general better than the average value, because, as a rule, the amplitudes are not symmetrical to the average value, i.e. they are not subject to a Gaussian distribution. The node values $M_2$ and $M_3$ are calculated analogously to $M_1$. For a coarser matching, one lower and one upper frequency-related node values $M_1$, $M_3$ may be sufficient, so that the calculation of the middle node $M_2$ can be omitted.

Figure 7:
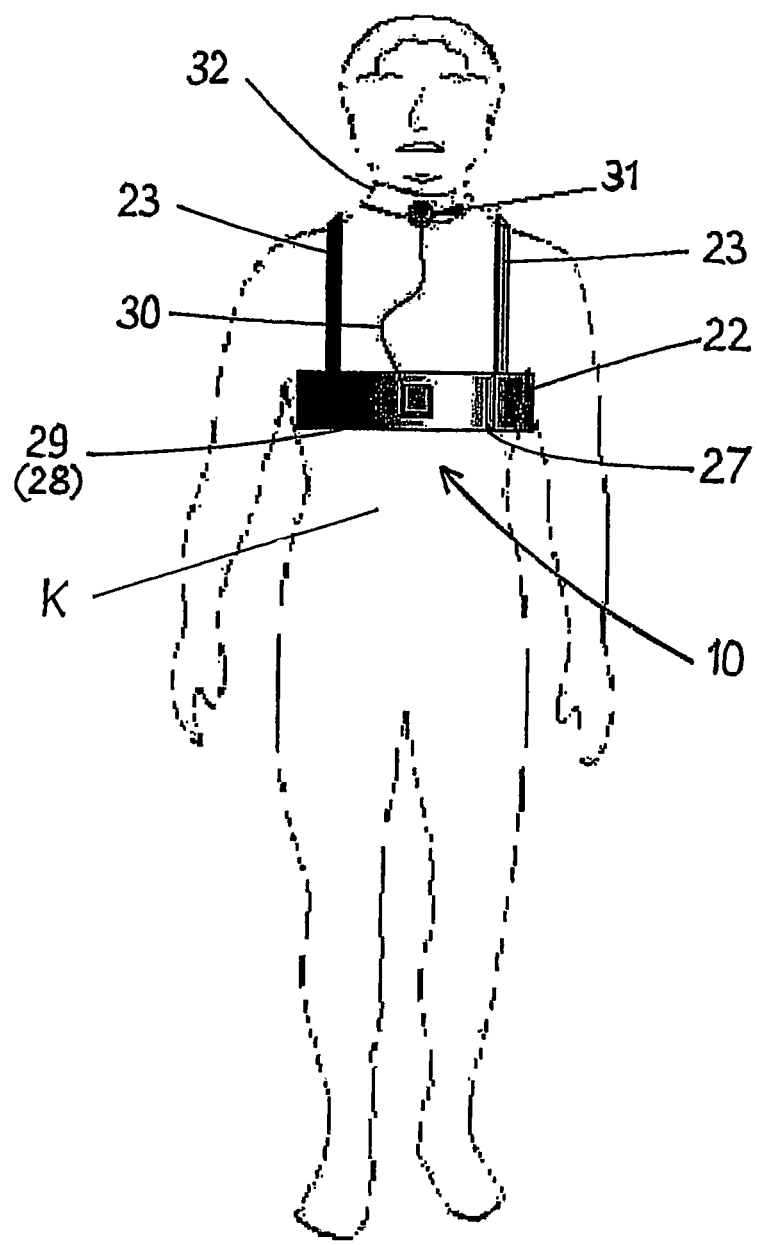
FIG. 7 is a schematic representation of the way of wearing a data logger.
Figure 8:
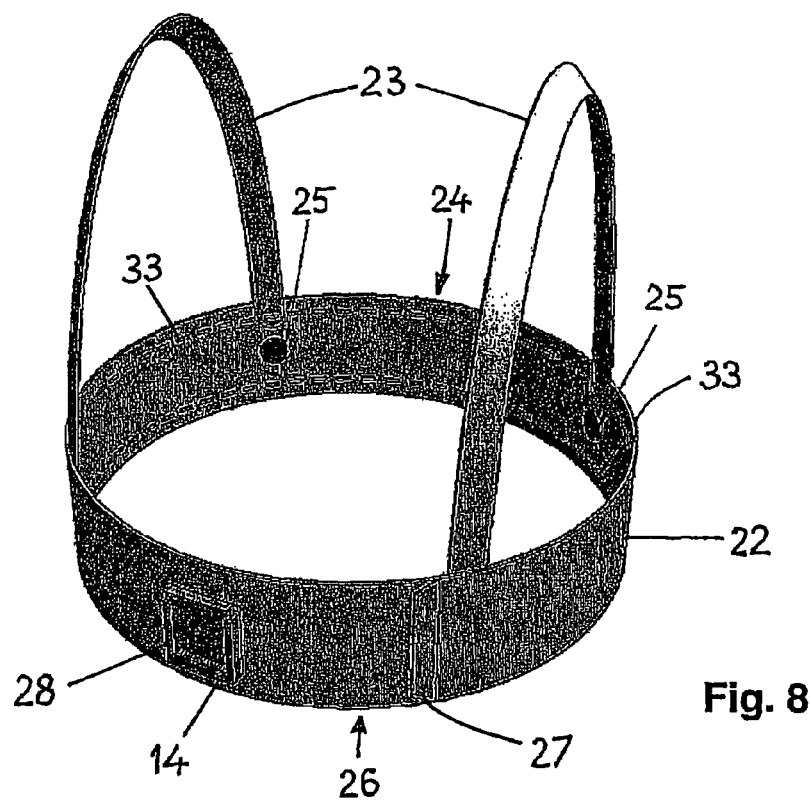
FIG. 8 is an oblique view of a wearing device.
Figure 9:
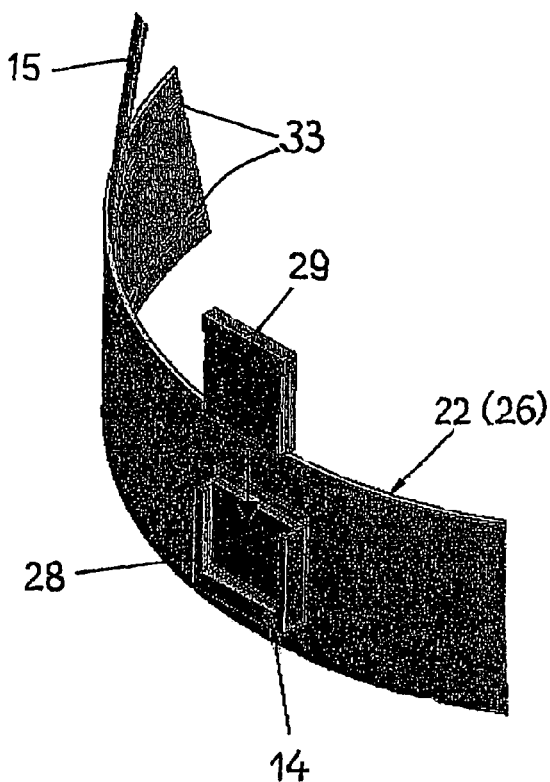
FIG. 9 is an enlarged detail of FIG. 8.

FIG. 7 shows schematically in which way a data logger 10 is fixed on the body K of an adult. FIGS. 8 and 9 show more clearly that a chest belt 22 provided with shoulder straps 23 and including in a back part 24 two microphones 25 is used for this purpose. On the front part 26 of the chest belt 22, which can be opened and closed by means of a Velcro fastener 27, there is a holder or receptacle 28 for a detachable data box 29, to which a feed line 30 from a tracheal microphone 31 is led. On the inner circumference of the chest belt 22, at least one respiration sensor 33 is integrated. Furthermore, an external microphone as an ambient sensor 14 can be provided, for example, on the receptacle 28.

The invention is not limited to any of the above-described embodiments, but can be modified in many ways. It is, however, recognizable that with an altogether low expenditure, it enables a—stationary or mobile—long-term monitoring of, e.g., the respiration of patients, so that their lung sounds are detected and the corresponding measuring data are stored, which will be immediately available above all for an early detection of diseases and acute disorders. The same applies for the monitoring of intestinal sounds, which are very important for the evaluation of the peristalsis, e.g. for the early detection of a mechanical/paralytic ileus. For the clinical sector, the invention creates an early warning system with immediate signal generation, allowing doctors and nurses to take rapid action in case of an emergency, with requiring the operation of individual devices. The apparatus requires a maximum of three bioacoustic sensors (12), each of which can be fixed to a point of an object body (K) facing the examination area, a maximum of one sensor (14) for recording surrounding noises, a maximum of four separable channels (11) for recording and transmitting sound signals or sound data detected by the sensors (12), and devices for supplying power and for forwarding, converting, storing, and displaying sequences of signals or data on or in a recorder or a computer unit (20). The data logger (10) can be combined with a chest belt (22), which can be put on and taken off an object body (K) and which includes shoulder straps (23) to relieve the weight and, in particular on the back, two bioacoustic sensors (14; 25) as well as on the front a receptacle (28) for a data box (29) connected via a feed line (30) with a tracheal microphone (31).

All features and advantages, including constructional details, spatial arrangement and procedure steps which are evident from the claims, the description and the drawing can be essential for the invention both separately and in all possible combinations.

LIST OF REFERENCE NUMBERS

A Matching line
$M_1$ $M_2$ $M_3$ Median-based nodes
P Peak
S Spectral curve
1, 2, 3 Frequency ranges
10 Apparatus/data logger
12 Acoustic sensors
14 Ambient sensor
15 Cable 26 Front part
16 Amplifier box
18 Filter box
19 Analog-digital converter
20 Computer (unit)/laptop
21 Display/monitor
22 Chest belt
23 Strap
24 Back part
25 (Back) microphones
27 Velcro fastener
28 Receptacle/data-box holder
29 Data box
30 Feed line(s)
31 Tracheal microphone
32 Neck belt

The invention claimed is:

1. A method for detecting and monitoring body sounds in humans and animals, in which bioacoustics sensors and analyzers that are mounted downstream are used, wherein,
the bioacoustics sensors are fixed to a maximum of three points of an object body,
a maximum of one additional bioacoustics sensor is provided for recording surrounding noises,
the bioacoustics sensors continuously detect sound signals and/or sound data, within a selectable time segment,
sequences of the sound signals and/or sound data are digitized, stored, and converted into a plurality of frequency-dependent spectral curves,
a plurality of node-defined matching lines are continuously allocated to each corresponding frequency-dependent spectral curve, and
each node-defined matching line is compared with the corresponding frequency-dependent spectral curve for analyzable and signalizable identification of specific sound symptoms.

2. The method according to claim 1, wherein a conversion time window with resolutions of approximately 0.1 s is selected for converting the digitized sequences of the sound signals and/or sound data into the plurality of frequency-dependent spectral curves.

3. The method according to claim 1, wherein a Fourier transform or a fast Fourier transform of the data is affected in a spectral range, one spectral curve per conversion time window originating, with which amplitudes are represented over a frequency, transmitted and recorded.

4. The method according to claim 1, wherein from each spectral curve, at least two frequency ranges are selected and median values are determined, which correspond to nodes of the sequences of the sound signals and/or sound data, and that the allocated matching lines are developed on a basis of the nodes.

5. The method according to claim 1, wherein, when viewing the frequency-dependent spectral curves and the node-defined matching lines in an X, Y-coordinate axis system, each node value of the node-defined matching lines is an Y-amount at a frequency point X and that an analysis by comparing Y-values of the corresponding frequency-dependent spectral curve and of the corresponding node-defined matching line is effected by means of threshold values.

6. The method according to claim 1, wherein, for the frequency-dependent spectral curves, two partial frequency ranges are selected from a band of 150 Hz to 1,600 Hz, whose scope is determined by a multiple of an admissible signal peak width, which for humans lies in the range of 5 times to 0.5 times the admissible signal width.

7. The method according to claim 6, wherein the multiple of the admissible signal peak width corresponds to approximately 100 Hz to 200 Hz.

8. The method according to claim 1, wherein a control sensor for the oxygen content of the blood is fixed on the object body.

9. The method according to claim 1, wherein a detection of wheezing events from the frequency-dependent spectral curves is by an application of plausibility criteria based on secured measuring results, wherein:
i) a local maximum in a frequency range within a conversion time window is not wider than 100 Hz when a threshold-value is exceeded;
ii) a maxima detected lie within a frequency band between 150 Hz and 1,600 Hz;
iii) a frequency change of a strongest of a local maxima is less than 100 Hz between two successive conversion time windows;
iv) the wheezing events have a minimum length of more than 0.3 s;
v) the wheezing events do not last longer than double a time of a normal mean expiration phase of the humans and animals in question.

10. The method according to claim 9, wherein a combined wheezing rate is obtained for each of a plurality of diagnosis time segments by combining wheezing events detected by all body sensors, a rate relating to time portions of all events which were detected by at least one sensor of all sensors.

11. The method according to claim 9, wherein a wheezing event of the wheezing events detected is discarded as being an artifact if detected simultaneously in a channel for surrounding noises.

12. The method according to claim 1, wherein for cough detection from the frequency-dependent spectral curves, an occurrence of steep edges of an amplitude signal of a surrounding noise is analyzed under a condition that simultaneously large amplitudes or overshootings are detected in all other sound signals facing the object body.

13. The method according to claim 12, wherein cough sequences of said cough detection are formed and stored with summation and/or averaging over an entire measuring time and/or through time-dependency diagrams of maximum values.

14. An apparatus for carrying out a method for detecting and monitoring body sounds in humans and animals, in which bioacoustics sensors and analyzers that are mounted downstream are used, wherein, the bioacoustics sensors are fixed to a maximum of three points of an object body, a maximum of one additional bioacoustics sensor is provided for recording surrounding noises, the bioacoustics sensors continuously detect sound signals and/or sound data, within a selectable time segment, sequences of the sound signals and/or sound data are digitized, stored, and converted into a plurality of frequency-dependent spectral curves, a plurality of node-defined matching lines are continuously allocated to each corresponding frequency-dependent spectral curve, each node-defined matching line are compared with the corresponding frequency-dependent spectral curve for analyzable and signalizable identification of specific sound symptoms, and wherein the apparatus further comprises, a maximum of three bioacoustics sensors, each of which can be fixed to a point of an object body facing an examination area, a maximum of one sensor for recording surrounding noises, a maximum of four separable channels for recording and transmitting the sound signals or sound data detected by any of the sensors, and devices for supplying power and for forwarding, converting, storing, and displaying the sequences of the sound signals or sound data on or in a recorder or a computer unit.

15. The apparatus according to claim 14, wherein in addition to the bioacoustics sensors, a position sensor is provided.

16. The apparatus according to claim 14, wherein in addition, a sensor for scanning movements of a thorax is provided, for recording a respiration.

17. The apparatus according to claim 16, wherein for fixing on an upper part of the body, a chest belt is provided.

18. The apparatus according to claim 14, wherein the bioacoustics sensors are air-coupled or piezo microphones.

19. The apparatus according to claim 14, wherein on or in the bioacoustics sensors or in telecontrol connection therewith, analog-digital converters are provided, whose output supplies digital signals or signal sequences.

20. The apparatus according to claim 14, wherein a preamplifier and/or an analog filter is allocated to one or more of the bioacoustics sensors.

21. The apparatus according to claim 19, wherein at least one transmitter is provided for signals transmitted by any of the bioacoustics sensors and/or analog-digital converters, which is coupled with a data memory and/or a transfer device.

22. The apparatus according to claim 14, wherein devices for a Fourier transform or fast Fourier transform are provided.

23. The apparatus according to claim 14, wherein the maximum of three bioacoustics sensors, the maximum of one sensor, the maximum of four separable channels, and the devices are integrated or can be integrated in a housing, or a case.

24. The apparatus according to claim 14, wherein the apparatus is a data logger which can be worn on the body and which can be used in an individual, ambulatory or stationary manner.

25. The apparatus according to claim 24, wherein the data logger is provided with acoustic micromemories.

26. The apparatus according to claim 24, wherein the data logger is provided with a chest belt, which can be put on and taken off an object body and which includes shoulder straps to relieve a weight, and wherein the data logger further includes two bioacoustics sensors of the bioacoustics sensors as well as, on a front of the data logger, a receptacle for a data box connected via a feed line with a tracheal microphone.

27. The apparatus according to claim 26, wherein on or next to the receptacle, an ambient sensor is arranged.

* * * * *